US00PP13851P39

(12) United States Plant Patent
Strauss et al.

(10) Patent No.: US PP13,851 P3
(45) Date of Patent: May 27, 2003

(54) MAGNOLIA PLANT NAMED 'STRGRA'

(75) Inventors: Edward V. Strauss, Silky Oaks (AU); Patricia A. Strauss, Silky Oaks (AU)

(73) Assignee: Leo Koelewyn, Victoria (AT)

( * ) Notice: Subject to any disclaimer, the term of this patent is extended or adjusted under 35 U.S.C. 154(b) by 0 days.

(21) Appl. No.: 09/874,300

(22) Filed: Jun. 6, 2001

(65) Prior Publication Data

US 2003/0024022 P1 Jan. 30, 2003

(51) Int. Cl.[7] ..... A01H 5/00
(52) U.S. Cl. ..... Plt./223
(58) Field of Search ..... Plt./223, 216

(56) References Cited

PUBLICATIONS

UPOV–ROM GTITM Computer Database 2002/03, GTI Jouve Retrieval Software, Citation for Magnolia 'Strgra'.*

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct cultivar of magnolia named 'STRgra' which is smaller in size than its maternal parent, has an early flowering habit, deep green glossy leaves RHS 146A, 6 month flowering period, and strong sweet lemony scent. The cultivar has a larger growth habit than the closest comparative cultivar *Magnolia grandiflora* 'Little Gem'.

3 Drawing Sheets

Latin Name of the Genus and Species of the Plant Claimed: *Magnolia grandiflora.*
Variety Denomination: 'STRgra'.

BACKGROUND OF THE INVENTION

The present invention comprises a new and distinct cultivar of *Magnolia grandiflora,* hereinafter referred to by the cultivar name 'STRgra' and having the common name Bull Bay Magnolia.

The new cultivar was isolated by the inventors at Uki, New South Wales, Australia, by seedling selection following self-pollination of the maternal parent, an unnamed plant of *Magnolia grandiflora.* The new cultivar was selected by the inventors, Edward V. Strauss and Patricia A. Strauss, primarily for its small size and early flowering habit. The new cultivar is distinguished from the maternal parent by its medium leaf size, small spreading growth habit, early flowering and medium flower size.

Following selection of the seedling, the cultivar was grown from cuttings propagated vegetatively by grafting. Following several generations of propagated cuttings, uniformity and stability of the selected characteristics was observed. Horticultural examination of the instant plant has demonstrated that the combination of characteristics herein disclosed for 'STRgra' are firmly fixed and are retained through successive generations of asexual reproduction.

The selected seedling was observed to flower in its second year, and was very florific over a long flowering season with smaller leaves and a small multi-branched plant habit about one third of the size of its sister seedlings. The following table of characteristics indicate the manner in which the new cultivar is distinct.

TABLE 1

| | Leaf Size | Tree Shape | Early Flowering | Flower Size | Underside of Leaf |
|---|---|---|---|---|---|
| Maternal Parent: *Magnolia grandiflora* | Large | Tall Spreading | No | Large | Light Variable |
| Comparative Cultivar: *Magnolia grandiflora* 'Little Gem' | Small | Medium Upright | Yes | Small | Heavy |
| Present Cultivar: *Magnolia grandiflora* 'STRgra' | Medium | Small Spreading | Yes | Medium | Light |

BRIEF DESCRIPTION OF THE INVENTION

The following traits have been repeatedly observed and are determined to be basic characteristics of 'STRgra' which, in combination, distinguish this Magnolia as a new and distinct cultivar:

1. Early flowering habit;
2. Deep, green glossy leaves, RHS 146A;
3. 6 month flowering period; and
4. Strong, sweet, lemony scent.

'STRgra' has not been observed under all possible environmental conditions.

The phenotype of the new cultivar may vary significantly with variations in environment such as temperature, light intensity, and day length without any change in genotype. The following observations, measurements, and values describe the new cultivar as grown in Uki, New South Wales, Australia under conditions which approximate those generally used in commercial practice.

BRIEF DESCRIPTION OF THE DRAWINGS

The accompanying color photographs show typical flowers and foliage of an 8–10 year old 'STRgra' plant, with colors being as true as possible with illustrations of this type.

The first photographic drawing shows a flower and foliage of 'STRgra'.

The second photographic drawing shows a close-up of the flower bud and foliage of 'STRgra'.

The third photographic drawing shows an immature flower bud and foliage of 'STRgra'.

DETAILED BOTANICAL DESCRIPTION

Color references are made to The Royal Horticultural Society Colour Chart (R.H.S.) except where general colors of ordinary significance are used. Colors are approximate as color depends on horticultural practices such as light level and fertilization rate, among other things. The age of the plant as described is 8–10 years.

Origin: Seedling from breeding program.

Parentage:

*Female parent.*—Unnamed plant of *Magnolia grandiflora.*

Propagation: Plants have been selected from the original seedling and propagated vegetatively by grafting in Monbulk, VIC, Australia.

Plant:

*Growth rate.*—Slow growth rate. From vegetative propagation flowering immediately.

*Flowering season.*—Flowering from Spring to Autumn in subtropics; summer to Autumn in temperate climate.

*Density.*—Thick.

*Growth type.*—Bush.

*Height.*—2000–2500 mm in 10 years.

*Width.*—2000–2500 mm in 10 years.

*Stem.*—4–6 mm diameter; smooth surface texture.

*Lenticels.*—Small, 1 mm; RHS 199D.

*Branching arrangement.*—Whorled.

Leaf:

*Petiole.*—Average length 15 mm; RHS 151A.

*Color.*—Deep green on top (glossy) RHS 146A, underside of leaf is RHS 152A.

*Length.*—150–170 mm.

*Width.*—65–70 mm.

*Apex.*—Acute, cuneate.

*Margin.*—Entire, slightly recurved.

*Mid rib.*—Creamy yellow RHS 8C, prominently raised below deep green RHS 136A.

*Texture.*—Glabrous, lustrous, and glossy (upperside), hairy (underside).

*Shape.*—Oblanceolate.

*Arrangement.*—Alternate.

Flower:

*Length of flowering period.*—Long, 6 months (depending on climate).

*Diameter.*—130 mm.

*Shape.*—Cup-shaped.

*Flower profile upper.*—Cup shaped, upper wider than lower.

*Flower profile lower.*—Cup shaped, narrowing at base.

*Number of flowers.*—1 per flowering stem.

*Lastingness of bloom.*—Flowers last approximately 3 days.

*Color midzone outside.*—Creamy-white RHS 155A.

*Midzone inside.*—Creamy-white RHS 155A.

*Margin inside.*—Creamy-white RHS 155A.

*Buds.*—Bud shape: Ovate, spear-shaped. Length: 70 mm. Width: 30 mm. Color: Flower buds encased in hairy pods which split to open, creamy-white RHS 155A.

*Petals.*—Number of petals: 6–9. Length: 85 mm. Width: 75 mm. Arrangement: Overlapping.

*Peduncle.*—Prickles: None. Length: 55 mm. Color: RHS 164B.

*Sepals.*—Number: 3. Color: RHS 157D. Extensions: Weak. Length: 90 mm. Width: 60 mm.

*Basal spot.*—None.

*Stamen.*—Approximately 240.

*Filament color.*—Light yellow 8C, 21 mm in length.

*Anther color.*—Limey-cream RHS 1B.

*Style.*—Cream RHS 155B, base color RHS 59A; 40 mm long.

*Pistils.*—Approximately 67 in an erect cone, color limey-cream RHS 1B.

Seed vessel characteristics:

*Size.*—Medium.

*Color.*—Pale green RHS 145B.

Fruit: Terminal cone approximately one or seeded carpets; scarlet RHS 60B when ripe.

Fragrance of bloom: Typical fragrance of *Magnolia grandiflora* but stronger, sweet lemony scent.

I claim:

1. A new and distinct Magnolia plant named 'STRgra', as illustrated and as described.

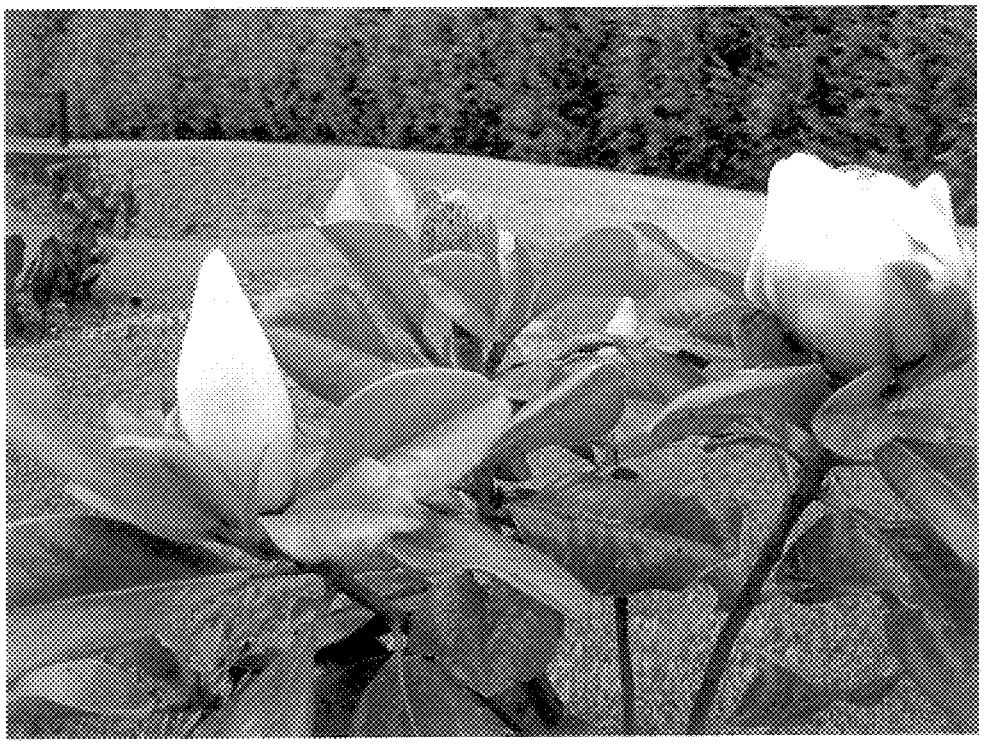

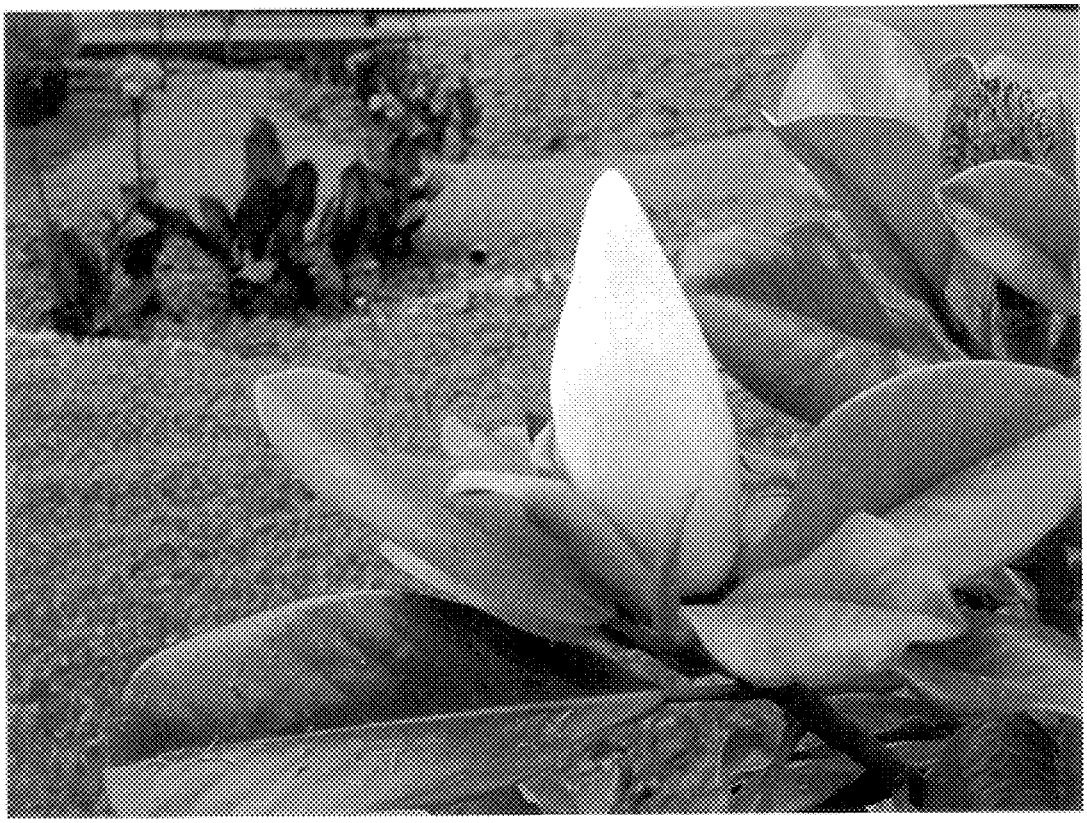

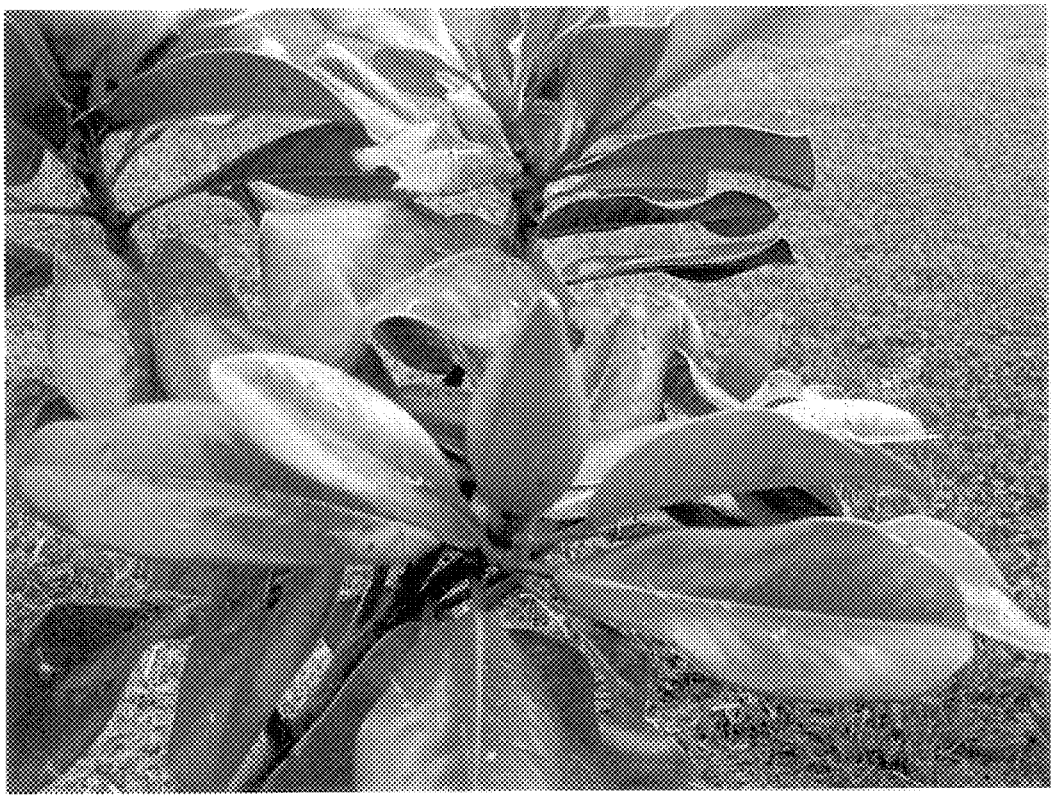

* * * * *